United States Patent
Hancock et al.

(10) Patent No.: US 9,308,285 B2
(45) Date of Patent: Apr. 12, 2016

(54) GAS PLASMA DISINFECTION AND STERILISATION APPARATUS

(71) Applicant: CREO MEDICAL LIMITED, Chepstow, Gwent (GB)

(72) Inventors: Christopher Paul Hancock, Bath (GB); Steven Morris, Bath (GB)

(73) Assignee: CREO MEDICAL LIMITED, Chepstow (GB)

( * ) Notice: Subject to any disclaimer, the term of this patent is extended or adjusted under 35 U.S.C. 154(b) by 134 days.

(21) Appl. No.: 14/360,593

(22) PCT Filed: Nov. 14, 2012

(86) PCT No.: PCT/GB2012/052822
§ 371 (c)(1),
(2) Date: May 23, 2014

(87) PCT Pub. No.: WO2013/076458
PCT Pub. Date: May 30, 2013

(65) Prior Publication Data
US 2014/0319382 A1    Oct. 30, 2014

(30) Foreign Application Priority Data
Nov. 24, 2011    (GB) .................................. 1120278.5

(51) Int. Cl.
*A61L 2/14*    (2006.01)
*H05H 1/46*    (2006.01)

(52) U.S. Cl.
CPC .. *A61L 2/14* (2013.01); *H05H 1/46* (2013.01); *H05H 2001/463* (2013.01); *H05H 2240/20* (2013.01); *H05H 2245/1225* (2013.01)

(58) Field of Classification Search
CPC ...... A61L 2/14; H05H 1/46; H05H 2001/463; H05H 2240/20; H05H 2245/1225
See application file for complete search history.

(56) References Cited

U.S. PATENT DOCUMENTS

2007/0193517 A1    8/2007    Matsuuchi et al.

FOREIGN PATENT DOCUMENTS

| EP | 0 395 415 A2 | 10/1990 |
|---|---|---|
| EP | 1 765 044 A1 | 3/2007 |
| WO | WO 2009/060213 A1 | 5/2009 |

OTHER PUBLICATIONS

International Search Report, International Application No. PCT/GB2012/052822 mailing date May 27, 2013.

*Primary Examiner* — Kishor Mayekar
(74) *Attorney, Agent, or Firm* — Arent Fox LLP

(57) ABSTRACT

A sterilization or disinfecting system in which non-thermal plasma is generated in pulses, in which pulses of microwave frequency energy are used to sustain each plasma pulse, and a detectable characteristic of each pulse of microwave energy is used to trigger a radiofrequency strike pulse which strikes the plasma. The system includes a strike signal generation circuit arranged to condition and/or process the signal from the microwave signal coupler to form a control signal based on the detectable characteristic, which may be the rising edge or amplitude of the pulse.

28 Claims, 8 Drawing Sheets

GAS PLASMA DISINFECTION AND STERILISATION APPARATUS

CROSS-REFERENCED TO RELATED APPLICATIONS

This application is a National Stage entry of International Application PCT/GB2012/052822 filed Nov. 14, 2012, which claims priority to British Application No. 1120278.5, filed Nov. 24, 2011, the disclosure of each of these prior applications being hereby incorporated in their entirety by reference.

FIELD OF THE INVENTION

This invention relates to sterilisation and/or disinfection systems suitable for clinical use, e.g. on or in the human or animal body. For example, the invention may provide a system that can be used to destroy or treat certain bacteria and/or viruses associated with the human or animal biological system and/or the surrounding environment. In particular, the invention may be suitable for the sterilisation and/or disinfection of a user's hands, e.g. in a clinical environment such as a hospital, doctor's surgery or the like. This equipment may also be used in the food industry for disinfecting or sterilising workers hands or food or packaging.

BACKGROUND TO THE INVENTION

Sterilisation is an act or process that destroys or eliminates microscopic forms of life, e.g. micro-organisms, bacteria, etc. During the process of plasma sterilisation, active agents are produced. These active agents may include high intensity ultraviolet photons and free radicals, which are atoms or assemblies of atoms with chemically unpaired electrons. An attractive feature of plasma sterilisation is that it is possible to achieve sterilisation at relatively low temperatures, such as body temperature. Plasma sterilisation also has the benefit that it is safe to the operator and the patient. In the case of hand disinfection, the cool plasma may be used instead of alcohol gel, the repeated use of which can cause a number of skin related problems.

Low temperature atmospheric pressure plasmas may be used to replace conventional sterilisation methods and offer clear advantage over existing means of sterilisation in terms of their non-toxic nature, instant treatment effects, and the ability to produce the plasma at a range of energy levels and in a range of different forms. In a room temperature environment, plasma is usually supported by electro-magnetic (EM) fields. Electrons absorb energy from an electric field and transfer part of this energy to heavy particles in the plasma. If electrons are not given sufficient opportunity to transfer their energy, heavier plasma components remain at much lower temperatures than the electrons. Such plasmas are called non-thermal plasma and their gas temperatures can be as low as room temperature.

A non-thermal plasma can be used to create highly reactive plasma particles (including e.g. electrons, ions, radicals, and other chemically active species) and ultraviolet (UV) radiation, which in turn may be used to disinfect and sterilise biological tissue, external work surfaces or surgical instruments. For example, UV photons in the plasma may affect bacteria cells by inducing the formation of thymine dimers in their DNA. This inhibits the ability of the bacteria to replicate properly. This effect may be particularly useful where it is desirable to reduce the level of bacteria, but not totally destroy it, i.e. so as not to destroy the body's natural flora.

The closer the plasma source is located with respect to the biological tissue (or other surfaces) and the higher the electric field in the plasma, the higher the intensity and efficacy of the non-thermal plasma sterilisation treatment process.

WO 2009/060213 discloses a sterilisation system having a controllable (e.g. capable of modulation in an adjustable manner) non-ionising microwave radiation source for providing microwave energy for combining with a gas (e.g. an inert gas or a mixture of inert gases) to produce atmospheric plasma. One example of the system described therein included a power splitting unit arranged to split microwave energy (e.g. from a microwave feed structure such as a co-axial cable) between a plurality of plasma generating regions, wherein a gas feed was connected to deliver gas to each plasma generating region, and in which the outlets of the plurality of plasma generating regions were spatially arranged to deliver a substantially uniform blanket or line of plasma from a plurality of plasmas generated in each respective plasma generating region. It was contemplated to provide ten or more plasma generating regions housed in a frame defining an aperture, wherein the plasmas from the plasma generating regions were directed inwards from the frame to provide a blanket of plasma for items passed through the frame. In particular, this application described an apparatus for sterilising hands in which movable plasma jets were provided in a box in which the hands could be inserted.

To strike plasma it is desirable to have a high electric field (e.g. high voltage or high impedance condition). Accordingly, it is necessary to set-up a high impedance state in order to enable the high voltage (high electric field) necessary to break down the gas to be generated. In one embodiment discussed in WO 2009/060213, the high voltage (high impedance) condition is set up using a flyback circuit that uses a low frequency (e.g. radiofrequency) oscillator circuit and a transformer whose primary winding is connected to the low voltage oscillator circuit by a suitable driver and switching device (e.g. gate drive chip and a power MOSFET or BJT). The arrangement generates high voltage pulses or spikes which strike or otherwise initiate the plasma.

After the plasma is struck, the impedance seen by the microwave power feed structure changes due to the change of the non-conducting gas into the conducting plasma. Here it is desirable to efficiently deliver the microwave energy into the plasma in order to sustain it. It is desirable for all (or most of) the microwave energy to be coupled into the plasma. Accordingly, it is desirable to match the generator impedance (i.e. the impedance of the microwave power feed structure) to the impedance of the plasma.

SUMMARY OF THE INVENTION

The present invention builds on the disclosure of WO 2009/060213 to provide a gas plasma sterilisation apparatus that may be particularly suitable from the perspective of cost effectiveness and user safety for incorporating into a mass-produced hand sterilising or disinfecting appliance.

At its most general, the invention proposes a sterilisation or disinfecting system in which non-thermal plasma is generated in pulses, wherein each pulse of microwave frequency energy used to sustain each plasma pulse is used to trigger a radiofrequency strike pulse which strikes the plasma. By synchronising the strike pulse and sustain pulse in this manner, the invention may increase the certainty of each plasma strike and may enable efficient energy delivery into the plasma, which in turn provides the energy for sterilisation or disinfection.

According to the invention, there may be provided plasma sterilisation apparatus (i.e. a non-thermal plasma generating apparatus for sterilising or disinfecting surfaces) comprising: a microwave cavity connectable to receive pulses of microwave frequency radiation from a microwave source; a plurality of microwave couplers, each microwave coupler being arranged to couple microwave energy out of the microwave cavity to a respective plasma strike zone, each plasma strike zone having a gas flow path therethrough; a gas feed connectable to supply ionisable gas to each gas flow path; and a strike signal generation circuit arranged to deliver a pulse of radiofrequency (RF) energy to each plasma strike zone to generate a high electric field therein for striking a non-thermal plasma in ionisable gas present on the gas flow path, wherein the strike signal generation circuit includes control circuitry arranged to use a detectable characteristic of a pulse of microwave frequency radiation received in the microwave cavity to trigger generation of the pulse of RF energy. The presence of a plurality of plasma strike zones enables the apparatus to emit a region of plasma that covers a wider area than may be possible with a single plasma jet.

The present invention thus proposes the use of different signals (e.g. from different sources) for striking the plasma and sustaining it, but synchronises these sources to increase certainty that microwave energy is delivered to the cavity only when a plasma is present.

In this specification "microwave frequency" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. 100 kHz to 500 kHz.

The microwave cavity may be any suitable enclosure for supporting an electromagnetic field corresponding to the received pulses of microwave frequency radiation. The microwave cavity may comprises a length of waveguide having a size to support propagation of the received microwave frequency radiation in the $TE_{10}$ mode. For example, for microwave frequencies around 2.45 GHz, a WR340 waveguide may be used. The length of the cavity may correspond to a whole number of half wavelengths of the microwave frequency radiation to be supported. For example, the cavity may have an operating length of around 250 mm for microwave frequencies around 2.45 GHz.

The microwave cavity may have an input located to correspond to a field maximum of the electromagnetic field supported thereby. For example, the input may be located at a distance corresponding to a odd multiple quarter wavelength from a closed (or shorted) end of the cavity. The input may comprise a suitable SMA or N-type connector, e.g. for connecting to a microwave feed cable (e.g. a flexible coaxial line or waveguide) that carries the pulses of microwave frequency radiation from the source. The input may also comprise a direct launch from the magnetron (or other, i.e. travelling wave tube) source, i.e. a quarter wave monopole (or loop antenna) coupled (or connected) directly into the waveguide section. For example, the quarter wave monopole may be connected into the waveguide cavity a distance of a quarter wavelength (or odd multiple thereof) from the shorted wall of the waveguide cavity.

The microwave source may have an output power capable of delivering into the microwave cavity microwave frequency radiation having an average power of 50 W or more. The delivered power level may be less than the output power level because of losses in the microwave feed cable and input connector, etc. For example, if the total loss between the microwave source and the microwave cavity were 3 dB, the output power of the microwave source would be at least 100 W in order to achieve an average power of 50 W in the cavity.

The microwave source may be a magnetron, which may be coupled directly into the cavity in order to overcome unnecessary cable loss, i.e. the insertion loss of the cable. It may be possible to have more than one source for each cavity, e.g. the microwave cavity may comprise a plurality of inputs, each input providing microwave frequency radiation from a respective source (e.g. magnetron, travelling wave tube, Klystron, or solid state source).

The microwave source may include a switching device for pulsing the microwave frequency radiation. In one embodiment, the switching device may be arranged to deliver pulses of microwave frequency radiation having duration of 40 ms and a duty cycle of 2/7, i.e. a cycle comprising an ON period of 40 ms followed by an OFF period of 100 ms. In this embodiment, the plasma may be struck using a 1 ms burst of 100 kHz RF energy, with an amplitude of around 400 V peak, where the burst of RF energy is synchronised to the leading edge of the microwave pulse. Using a peak power of around 50 W, this treatment profile is effective in the treatment of *Clostridium difficile* in the spore and vegetative states.

Herein, "pulse of RE energy" means transmission of RF energy for a discrete period of time, e.g. 10 ms or less, preferably 1 ms. This discrete period of RF energy transmission may also be referred to as a burst of RF energy. Each pulse of RF energy may comprise a plurality of bursts of RF energy. To trigger the pulse of RF energy (also referred to herein as the RF strike pulse), the apparatus may include a microwave signal coupler connected at a microwave signal input to the microwave cavity (e.g. the input discussed above) to couple a portion of the microwave frequency radiation received at the cavity (i.e. portion of the pulse of microwave frequency radiation) to the control circuitry of the strike signal generation circuit. The microwave signal coupler may be a directional coupler, e.g. a 10 dB forward directional coupler.

The strike signal generation circuit may be arranged to condition and/or process the signal from the microwave signal coupler to form a control signal (gating signal) based on the detectable characteristic of the pulse of microwave frequency radiation. The control signal is used by the strike signal generation circuit to generate the RF strike pulse or a burst of RF strike pulses. The detectable characteristic may be the rising edge of the pulse of microwave radiation. Alternatively it may be the amplitude of the pulse or the falling edge of the pulse.

The control circuitry may include a threshold comparator and a differentiator arranged to transform the signal from the microwave signal coupler into a pulse. The control circuitry may be implemented through an analogue circuit arrangement, where the width of said pulse is related to the C-R time constant of a single pole differentiator circuit and the reference voltage on the inverting pin of a threshold comparator that follows the differentiator. The microwave energy coupled out of the microwave cavity by the microwave signal coupler may be conditioned by a microwave detector before sending to the threshold comparator. The microwave detector may be a Schottky or tunnel diode having a response time of 100 ns or less, e.g. 10 ns to 100 ns, which can be fast enough to enable the rest of the circuit to function correctly.

For generating the RF strike pulse from the control signal, the strike signal generation circuit may comprise an continuous RF source (e.g. a gated free running oscillator), a MOSFET gate driver, a power MOSFET and a transformer with a turns ratio greater than unity. For example, a turns ratio of 1:100 may enable 10 V on the primary winding to provide 1000 V on the secondary winding for use in striking the plasma. The particular power MOSFET used may be selected in terms of its maximum voltage, current rating and turn on/off times.

The control signal may be logically combined (e.g. using an AND gate) with the output from the continuous RF source to generate a pulsed RF signal for use as an input to the gate driver circuit, which in turn is used to switch the power MOSFET to produce a voltage across the primary winding of the transformer. The control circuitry may be arranged to set the duration of the control signal to 10 ms or less. Thus, the duration of the burst of RF energy may be 10 ms or less, e.g. 1 ms.

If the duration of the control is 10 ms and the oscillator is free running at a frequency of 100 kHz, and the duty cycle is 50%, then RF strike pulse will comprise a burst of pulses with an ON time of 5 μs and an OFF time of 5 μs generated for a period of 10 ms. In other words, one thousand 5 μs RF pulses will be generated following the leading edge of each burst of microwave energy. The trigger for the one thousand RF pulses to commence will come from the leading edge of pulse derived from the burst of microwave energy that has been coupled and rectified.

In other embodiments, the pulsed RF signal may be triggered by a control signal from a microprocessor or the like, which may be arranged to detect the portion of the microwave frequency radiation coupled from the cavity (e.g. via a diode detector or a heterodyne/homodyne detector or the like). The differentiator discussed above may be realised in hardware or software.

The strike signal generation circuit may comprise a plurality of RF strike circuits, where each RF strike circuit comprises a gate driver, a power MOSFET and a transformer, and is arranged to deliver an RF strike pulse to a respective plasma strike zone. The plurality of RF strike circuits may share a the same continuous RF source (e.g. low voltage oscillator) or may each have their own RF source). The plurality of RF strike circuits may however receive a common input, i.e. the control signal discussed above. For example, the control circuitry may comprise a RF signal splitter arranged to split the control signal to generate a separate input signal for each RF strike circuit.

The plurality of microwave couplers may be arranged in one or more rows (e.g. in a rectangular array) on the microwave cavity. In one embodiment, each row has seven microwave couplers. The RF strike pulse for each row may be sequenced in such a manner that the plasma appears to be continuous, i.e. rows of plasma may be separately initiated using a strike pulse. There may be a delay between the initiation of the first row and the second row, and the second row and third row, and so on. The delay between consecutive strike pulses may be, for example, 100 μs or 1 ms. Taking this scenario, if the array comprises ten rows, then the whole array will be emitting plasma in a time frame of 1 ms or 10 ms respectively (i.e. quasi-continuous operation). An advantage of this arrangement is that it reduces the power required from the microwave source.

The strike pulse may be multiplexed using a suitable relay or MOSFET/BJT arrangement. Alternatively, a separate RF strike pulse circuit may be connected to each row of plasma and the drive signal to each plasma strike circuit may be sequenced using by introducing a time delay between adjacent drive signals, i.e. the low power RF oscillator may be applied to the first RF strike circuit 1 ms prior to the being applied to the second RF strike circuit, hence the second row of plasma is initiated 1 ms after the first row.

Each plasma strike zone may be located outside the microwave cavity. Each plasma strike zone may be defined by a pair of conductors between which it is possible to develop a high voltage, thereby generating the high electric field. The conductors of each plasma strike zone may be connectable to its respective RF strike circuit. As discussed above, the output of each RF strike circuit may be a gated burst of RF energy, e.g. a burst of sinusoidal high voltage RF pulses or spikes for a period of 1 ms. The peak voltage of the RF strike pulses may be 1 kV or more.

The RF strike circuit disclosed here is not limited to an arrangement that uses a MOSFET gate driver, power MOSFET and transformer. Other devices and circuit configurations that produce a burst or pulse of high voltage RF energy able to strike plasma in the required time frame may be used, e.g. a power bipolar junction transistor (BJT), a power Insulated gate bipolar transistor (IGBT), a thyristor, an auto transformer, an arrangement of voltage doubler circuits (Cockcroft stack) etc.

In one embodiment, each plasma strike zone comprises a dielectric conduit extending out of the microwave cavity and defining the gas flow path. The conduit may be made of a suitable low loss dielectric, such as quartz. Using a low loss dielectric ensures that the heat generated by the RF strike pulses is kept as low as possible. Each strike zone may include a coaxial arrangement comprising an inner conductor located inside the dielectric conduit and an outer conductor separated from the inner conductor by the dielectric conduit, wherein the strike signal generation circuit is connected to the coaxial arrangement to generate a high electric field within the dielectric conduit upon delivery of the pulse of radiofrequency (RF) energy (i.e. the RF strike pulse). The high electric field is thus generated between the inner and outer conductors. The dielectric conduit, if present, may inhibit arcing and may confine the ionisable gas flow within the high electric field. The gas feed may be arranged to introduce the gas to the plasma strike zone in this region. It is desirable for the gas flow path to travel through the position of the E field maximum generated by the RF strike pulse.

The RF strike circuit may be connected to the coaxial arrangement via a coaxial feed. The coaxial feed may comprise a grounded outer conductor electrically connected to the outer conductor of the coaxial arrangement and an active inner conductor electrically connected to the inner conductor of the coaxial arrangement. The active inner conductor may pass through an aperture in the dielectric conduit.

The coaxial feed may comprise a microwave blocking element arranged to protect the strike signal generation circuit from microwave energy in the plasma strike zone. In other words, the microwave blocking element can prevent microwave energy from being coupled out of the plasma strike zone by the inner conductor of the coaxial feed. The blocking element may also function to prevent the RF energy from radiating out of the circuit.

In one embodiment, the coaxial feed may comprise a coaxial output line having an inner conductor connected to the inner conductor of the coaxial arrangement and an outer conductor connected to the outer conductor of the coaxial arrangement, wherein the microwave blocking element comprises one or more quarter wavelength stubs and/or an inductor on or attached to the inner conductor of the coaxial output line. For a small scale device, it may be preferred to use an inductor because providing a quarter wavelength stub for each plasma strike zone may require too much space. To illustrate, a quarter wavelength stub for microwave frequency energy at 2.45 GHz in air has a length over 3 cm. If an inductor is used, it is preferably a wire wound inductor made of a low loss conductor such as silver, and preferably having a magnetic core.

In a preferred embodiment of the invention, the inner conductor of the coaxial arrangement is at least part of the microwave coupler for its respective plasma strike zone. This arrangement reduces the number of components in the plasma strike zone. The microwave coupler is discussed in more detail below.

Each microwave coupler may comprise a conductive member having a first portion protruding into a microwave cavity, i.e. a hollow rectangular or cylindrical section made from a low loss conductor (or a waveguide) and a second portion extending outwardly from the microwave cavity to its respective plasma strike zone, wherein the length of the first portion that is exposed in the microwave cavity is determined based on the field intensity of the microwave energy in the microwave cavity. With this arrangement it is possible to ensure that a desired amount of energy (e.g. an equal amount of energy at each coupler) is coupled out of the cavity. In a simple embodiment, the microwave couplers may be aligned with the field intensity maxima in the microwave cavity. In such an arrangement they would be spaced apart by half the loaded wavelength (i.e. the wavelength of the microwave frequency radiation guided by the microwave cavity). However, as microwave power is coupled out of the microwave cavity as the microwave frequency radiation propagates along the cavity away from the input, the field intensity decreases. Accordingly, it may be desirable to increase the amount of the first portion that is exposed in the microwave cavity for microwave couplers located further from the input relative to microwave couplers located closer to the input. With this configuration, the share of microwave power extracted by the microwave couplers may be equalised, which facilitates generation of a uniform plasma blanket.

Additionally or alternatively, in order to equalise the microwave power available at each plasma strike zone, it may be necessary to include an arrangement of tuning stubs inside the microwave cavity in order to change the field or field distribution set up inside the waveguide cavity. The tuning stubs may be on the same side/face as the microwave couplers, on the opposite side/face from the microwave couplers, or on one or both sides/faces orthogonal to the face/side where the microwave couplers are located. The tuning stubs may be adjustable. For example, they may comprise metallic or dielectric screws that protrude inside the cavity and whose length may be adjusted by mechanical means externally from the outside of the waveguide cavity. However, for mass-produced devices where the locations and lengths of the tuning stubs are already determined, the tuning stubs may be static tuning rods or posts.

In other embodiments it may be desirable for the microwave couplers to have a closer spacing, e.g. to allow the plasma strike zones (and ultimately the plasma jets emitted from the plasma strike zones) to be in close proximity to each other. Spacing adjacent microwave couplers by less than half the loaded wavelength may facilitate the generation of a "blanket" of plasma because the individual plasma jets may be brought closer together. Such a closer spacing inevitably means that the microwave couplers will not all align with field maxima in the microwave cavity. In this arrangement it may therefore be necessary to make further adaptations to the amount of the microwave couplers that are exposed in the microwave cavity, whereby the lower the field intensity the greater the amount of the first portion that is exposed.

The microwave cavity may be arranged to support substantially all the received microwave energy in a single waveguide mode (e.g. the $TE_{10}$ mode). With this arrangement there may be two factors governing the amount of the first portion that is exposed: (i) the distance of the microwave coupler from the nearest field maxima, and (ii) the distance of the microwave coupler from the input of the microwave frequency radiation to the microwave cavity. As these distances increase, so the amount of the first portion that needs to be exposed increases in order to achieve an equal share of coupled power. In other words, the amount of the first portion of each conductive member that is exposed in the microwave cavity is determined based on the position of its respective microwave coupler with respect to the field distribution of the waveguide mode and the distance between the microwave coupler and the location at which microwave energy is received in the cavity. Said coupler may be an E-field probe or an H-field loop arrangement.

The ionisable gas may be air or a suitable inert gas, e.g. argon. Preferably, the gas feed comprises a gas inlet for delivering gas to the gas flow path of each plasma strike zone at a location outside the microwave cavity. The gas may be piped into each individual plasma strike zone using a separate gas feed tube. Alternatively, the inlets may be interconnected (in series or parallel) to feed into a plurality of plasma strike zones, e.g. into a row of plasma strike zones. In such an arrangement, the gas feed system and the microwave energy feed system are separate from each other until the plasma strike zone itself. In other embodiments, however, it may be possible for the gas feed to include an inlet into the microwave cavity and a plurality of outlets from the microwave cavity, each outlet leading to a respective plasma strike zone, whereby the ionisable gas travels through the microwave cavity to reach the plasma strike zones. For example, each microwave coupler may be secured in the respective outlet of its plasma strike zone by a gas-permeable connector.

The plasma sterilisation apparatus discussed above may be incorporated in to a sterilising/disinfecting applicator for use in an appliance suitable for sterilising/disinfecting parts of the human body, in particular the hands. The appliance may comprise a housing have a recess therein for receiving a user's hands. One or more sterilising/disinfecting applicators may be mounted in the housing so that the plasma generated can be used to create active agents (e.g. ionised particles or other radicals) for sterilising the user's hands. In one embodiment there are four applicators in the appliance; one applicator for each side of each of the user's hands.

The active agents produced by the plasma can be distributed by using an array of plasma strike zones spread over a face of a single waveguide cavity. In an appliance with four applicators, there may be 100 or more plasma strike zones (e.g. 25 or more per applicator) to provide a desirable distribution. Alternatively, the active agents produced from a single plasma strike zone can be distributed by connecting the output of the plasma strike zone to a diffusion device. The diffusion device may be an enclosure chamber or box having an array of apertures in a surface thereof to allow the active species to flood out, e.g. into the recess of the appliance over the surface of the user's hands. For example, the diffusion device may be a rectangular box with the plasma source entering the top face and four holes in the bottom face to emit or deliver the species. This arrangement may enable the device to provide a blanket of active agents with fewer plasma strike zones.

To promote outward flow of the active agents, a blowing gas feed (which may use the same or a different gas from the plasma gas feed) may be connected to the diffusion device. A fan may also be provided to withdraw the active agents from the diffusion device.

In another embodiment, the gas may enter the waveguide cavity at a single inlet port and fill the waveguide cavity. The gas inside the waveguide cavity may then be used to enter each plasma generating region via slots or output ports in the waveguide cavity in the same location as the plasma generating regions. In this arrangement, the waveguide cavity may be partially sealed to allow the gas to only escape at the plasma generation regions, i.e. gas should not escape at the transition or interface between the waveguide cavity and the magnetron. In this arrangement, no plasma is generated inside the waveguide itself, i.e. plasma is only generated at the plasma strike zones.

BRIEF DESCRIPTION OF THE DRAWINGS

Embodiments of the invention are described in detail below with reference to the accompanying drawings, in which.

DETAILED DESCRIPTION; FURTHER OPTIONS AND PREFERENCES

Figure 1:
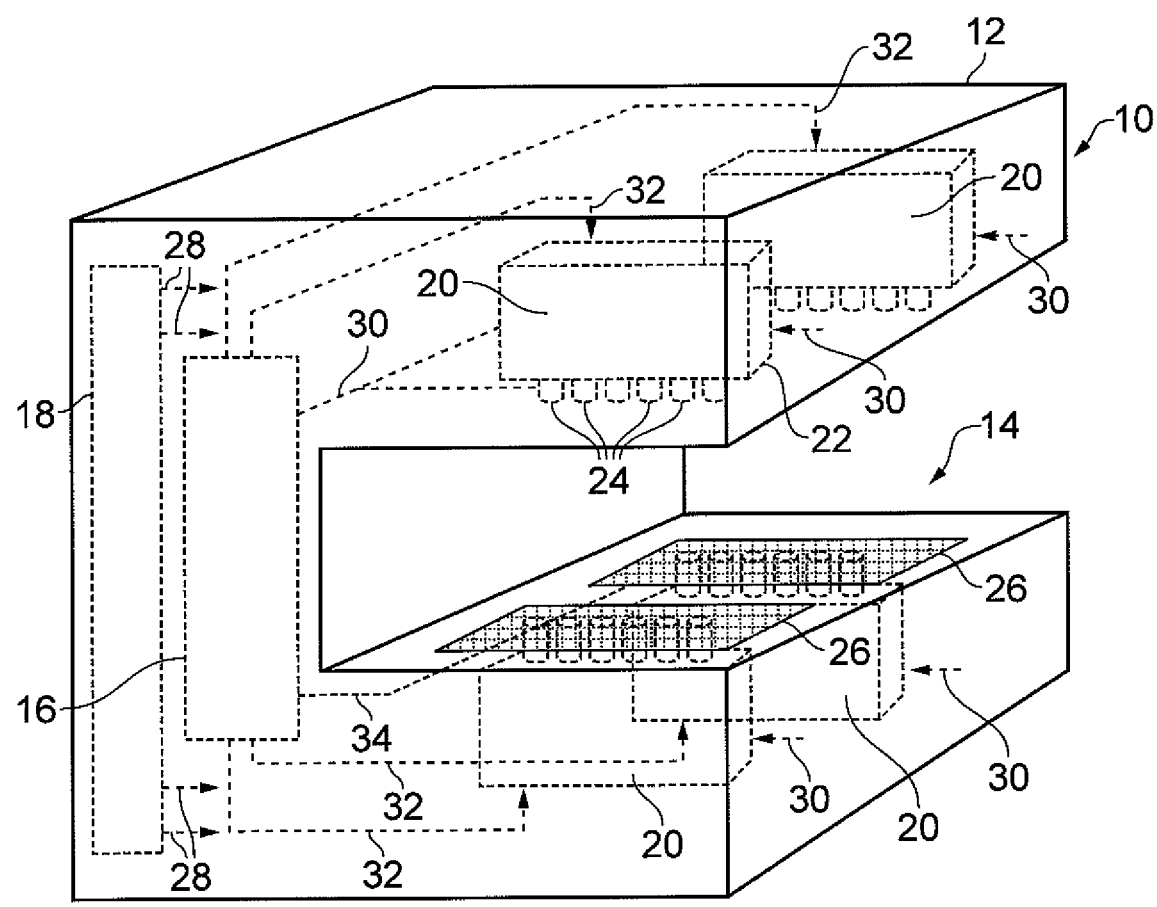
FIG. 1 is a schematic perspective view of an appliance for sterilising hands which incorporates plasma sterilising or disinfecting apparatus according to an embodiment of the invention.

FIG. 1 shows a hand sterilisation appliance 10 that incorporates the plasma sterilisation apparatus of the invention. The appliance 10 comprises a housing 12 which defines a recess 14 for receiving a user's hands (not shown). In this embodiment, the housing 12 comprises a U-shaped body, which the recess 14 being the space between the arms of the U. The housing 12 is a hollow casing that may contain the components of the system within it. For example, the housing 12 may contain a control module 16 which supplies and controls the energy for striking and sustaining the plasma used for sterilisation. The control module 16 may include a microwave power source (e.g. comprising one or more magnetrons) for generating microwave frequency radiation, strike signal generation circuitry for generating pulses of radiofrequency radiation (e.g. for striking the plasma) and control circuitry for controlling operation of the appliance as discussed below. The housing 12 may also contain a gas supply 18 for supplying inert gas (e.g. argon or the like). The housing 12 may be openable to permit replacement of the gas supply 18, which may be a single or plurality of gas bottles. It may be desirable to use more than one gas bottle in the system in order to ensure there is no downtime in device use, i.e. when one gas bottle becomes empty, a message is sent to the suppliers of gas bottles to connect a new bottle to the device.

The housing 12 also contains plasma sterilisation apparatus for generating and emitting plasma for sterilisation into the recess 14. In this embodiment, the plasma sterilisation apparatus comprises four plasma applicators 20. A pair of applicators is located adjacent each other in each arm of the U-shaped body. Each applicator 20 comprising a cuboidal microwave waveguide cavity 22 having a plurality (six in the embodiment) of quartz tubes 24 projecting from one face thereof. The applicators 20 are positioned so that the tubes 24 point towards the recess 14. The recess 14 may be exposed to the applicators 20 through meshed windows 26 in the inward facing walls of the housing 12. The size of the mesh may be selected to prevent the microwave energy from entering the recess 14 from the applicators 20.

In the arrangement shown in FIG. 1 each microwave cavity 22 is connected to receive microwave frequency radiation via a suitable feed structure 32 from a microwave source in the control module 16. Each cavity may have its own dedicated microwave source, e.g. comprising one or more magnetrons. Alternatively, a single microwave source (comprising one or more magnetrons) may supply microwave frequency radiation to all of the microwave cavities 22. The microwave source may be arranged to supply pulses of microwave energy. Where the applicators share a microwave source, the microwave energy may be supplied to each in turn, e.g. using a multiplexing technique.

The quartz tubes 24 may surround plasma strike zones as discussed in more detail below. Each plasma strike zone may be connected to receive pulses of RF radiation via a suitable feed structure 34 from the strike signal generation circuitry in the control module 16.

In this embodiment, the gas supply 18 is shown as having four outputs 28. Each output is connected by a gas feed conduit (not shown) to a respective input 30 for each applicator. In this embodiment, the inputs 30 communicate with the interior of each microwave cavity 22 whereby the gas travels along a gas flow path that passes through the cavity and exits the cavity through the quartz tubes 24. However, in other embodiments (e.g. discussed below with reference to FIG. 5) the gas flow path does not flow through the microwave cavity 22. Instead the input 30 for each applicator may comprise a plurality of inputs into the quartz tubes 24 directly.

In use, when a user's hands are inserted into the recess 14, the control module 16 is arranged to initiate the supply of gas from the gas supply 18 to the plasma strikes zones in the quartz tubes 24 and emit pulses of microwave frequency radiation from the microwave source(s) to the microwave cavities 22. The appliance 10 may include a motion or proximity detector (not shown) to detect the presence of an object in the recess to trigger operation. This type of technology is conventional in the field of hand drying appliances and is therefore not discussed in detail herein. According to the invention, each pulse of microwave energy delivered to the microwave cavities triggers the strike signal generation circuitry to supply an RF strike pulse to each plasma strike zone. As explained in more detail below, the timing of the RF strike pulse is controlled relative to the supply of gas and the microwave pulse such that the RF pulse serves to strike a non-thermal gas plasma in the gas present in the plasma strike zone e.g. by creating a high electric field within the quartz tube. The microwave pulse sustains the plasma, i.e. delivers its energy into the plasma to support the generation of active agents which are directed out of the housing 12 by the flow of gas. The active agents generated in the plasma act as sterilising or disinfecting agents to kill microorganisms present on the surface of objects (e.g. hands) in the recess 14.

Figure 2:
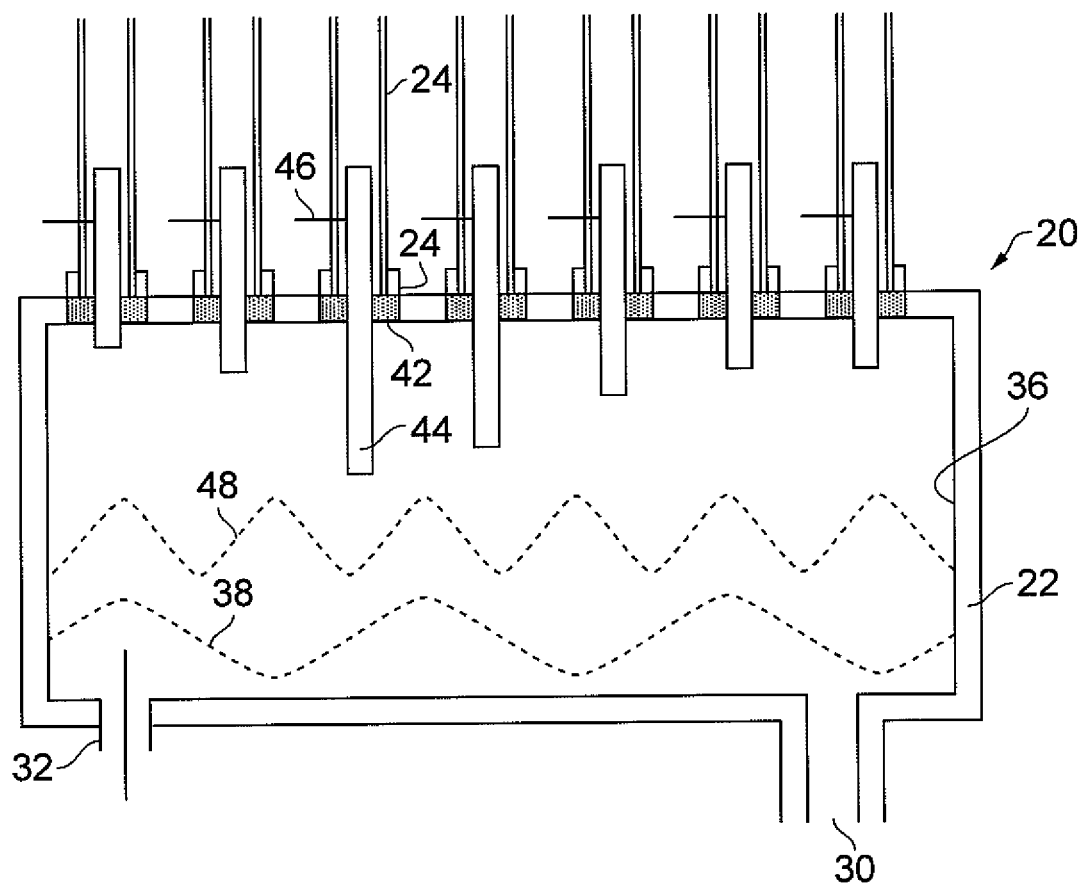
FIG. 2 is a schematic cross-sectional side view through plasma sterilisation apparatus that is an embodiment of the invention.

FIG. 2 shows a cross-sectional side view through a schematic representation of one of the plasma applicators 20 shown in FIG. 1. The plasma applicator 20 comprises a waveguide cavity 22 having an inner surface 36 made of conductive material (e.g. a metallised surface). The waveguide cavity 22 may be closed at both ends as illustrated in FIG. 2 or may have one end connected to a dummy load (not shown) to absorb any microwave energy that is not transferred to the gas plasma. In this embodiment, the microwave cavity has in its bottom face an microwave input 32 and a gas inlet 30. The microwave input 32 is connected by a suitable feed structure (e.g. flexible waveguide, coaxial feed or the like) to receive the microwave frequency radiation from the microwave source (e.g. magnetron, travelling wave tube, klystron or solid state source). The pulsed microwave frequency radiation is launched into the microwave cavity 22 by the microwave input 32. The microwave input 32 may comprise any suitable connecter, e.g. SMA or N-type connector or the like. In other embodiments, the microwave source may be connected directly to the waveguide cavity to avoid the need for a additional connectors. The gas inlet 30 is a simple conduit having a diameter less than one eighth of the wavelength at the frequency of operation to prevent microwave radiation from being radiated free space.

The microwave cavity 22 is preferably a cuboidal space dimensioned to support each pulse of the microwave frequency radiation in a fundamental mode, e.g. as a standing wave in the $TE_{10}$ mode. The length of the microwave cavity 22 is selected to be equal to a whole number of guided wavelengths (in this embodiment the length of the cavity is $3\lambda$, where $\lambda$ is the wavelength of microwave frequency radiation that is guided by the cavity). The microwave inlet 32 is positioned at a distance of $\lambda/4$ from one end of the cavity so that the microwave frequency radiation is launched where the guided E-field has a maximum intensity. The magnitude of the field intensity (the E-field) is illustrated in FIG. 2 schematically by dashed line 38. The field is at a minimum at the boundaries defined by ends of the cavity. In this embodiment there are three field maxima.

A plurality of quartz tubes 24 project away from the top face of the applicator 20. Each quartz tube 24 is secured to the microwave cavity 22 by an attachment portion 40, which may be a threaded wall or a suitable adhesive that is not absorbed by microwave energy, or a metal sleeve and a tight push fit. The quartz tube may extend through the surface of the waveguide cavity, but the centre conductor used in each plasma generation region must be shielded using a conductor that extends from the waveguide cavity to prevent radiation from the centre conductor. In this embodiment there are seven quartz tubes; in other embodiments there may be ten or more. In this embodiment, the quartz tubes are aligned along a single row on the top face of the applicator. In other embodiments the tubes may be distributed in an array, e.g. comprising a plurality of rows, across the top face of the applicator. For example, each waveguide applicator may be arranged to deliver seven rows of plasma, where each row contains seven plasma quartz tubes. Such a system will produce 49 jets of plasma.

Each quartz tube 24 defines an internal volume arranged to experience a high RF electric field (e.g. comprising a peak voltage of 150 V or more, i.e. 1 kV) caused by the RF strike pulse as explained below. This internal volume is also arranged to receive gas from the gas supply, whereby the high RF electric field is capable of striking a gas plasma. The internal volume is therefore referred to herein as the plasma strike zone. In this embodiment the plasma strike zone is a cylindrical region of space, but it may be any shape suitable for supporting the high RF electric field, i.e. it could be two parallel plates separated by a quartz glass sheet rather than a hollow cylindrical quartz tube with a first conductor on the inside and a second conductor on the outside.

In this embodiment, the gas supply is connected to inlet 30 to provide gas into the interior of the microwave cavity 22. This may load the microwave cavity 22 such that the guided wavelength is less that the wavelength in free space. The relative permittivity (dielectric constant) of the gas may thus need to be taken into account in order to ensure that the waveguide is dimensioned to support the fundamental mode, but as long as no plasma is created in this region, the effect caused by the gas within the region may be negligible and so the change in impedance may also be negligible. The length of the waveguide is preferably a whole number of wavelengths; the loaded wavelength $\lambda_l$ (i.e. wavelength when gas or other material, i.e. dielectric or magnetic loading material, is present) may be calculated as $$\lambda_l = \frac{c}{f\sqrt{\varepsilon_r}},$$

where c is the speed of light in a vacuum, f is the frequency of the microwave radiation input to the cavity, and $\varepsilon_r$ is the relative permittivity (dielectric constant) of the gas, or other material. It may be preferable to load or fill the waveguide cavity (or a portion of the waveguide cavity) with a dielectric or magnetic material in order to reduce the spacing between adjacent plasma generation regions placed across the waveguide and longitudinally (along or down the waveguide), i.e. across and along the top face of a rectangular waveguide section. Using loading material may enable adjacent plasma generation zones or regions to be brought closer together. For example, the pitch between adjacent probes may be reduced from 16 mm to 4 mm by loading the cavity with a low loss material that has a relative permittivity or relative permeability of 16.

The gas escapes from the microwave cavity 22 into each plasma strike zone via outlets 42 formed in the top face of the applicator 20. Each outlet 42 is located at the base of a corresponding quartz tube 24. The outlets 42 may comprise permeable PTFE rings which permit gas to flow therethrough but prevent the microwave radiation from escaping due to the size of the outlet, i.e. the diameter of a round coupling arrangement or the width of a slot. The gas is supplied under pressure to the cavity, which causes it to flow through the outlets 42 and along a flow path through the plasma strike zone and out of the end of the quartz tube. This gas flow transports active agents (i.e. high energy particles, free radicals and the like) out of the applicator (i.e. quartz tubes) where they can be used as sterilising agents. The active agents are created within the plasma strike zone by the plasma generated by each pulse of microwave frequency radiation. An embodiment in which the gas does not flow through the microwave cavity 22 is discussed below with reference to FIG. 5.

The gas plasma in each plasma strike zone is struck by a high voltage burst of RF energy, which may comprise one or more discrete pulses of RF energy. The RF strike pulse is supplied to a coaxial arrangement comprising an outer conductor (shown in FIG. 6) e.g. on the outer surface of the quartz tube 24, and an inner conductor mounted inside the plasma strike zone and separated from the outer conductor by the quartz tube itself. In this embodiment, the inner conductor is the microwave coupler 44 discussed in more detail below. An RF feed 46 (discussed in more detail with reference to FIG. 6 below) is connected to each coaxial arrangement. The RF feed 46 transfers the RF strike pulse from the strike signal generation circuit (discussed below with reference to FIG. 3) to the plasma strike zone.

As explained below, each RF strike pulse is triggered by sending a pulse of microwave frequency radiation to the microwave cavity. After the plasma is struck by the RF strike pulse, the applicator is arranged to couple power from the pulse of microwave frequency radiation in the cavity to sustain the plasma, which in turn causes the active agents useful for sterilisation to be created. Each RF strike pulse may itself also be responsible for creating some active agents. The microwave power is extracted from the microwave cavity 22 into each plasma strike zone by a corresponding microwave coupler 44. Each microwave coupler 44 is an elongate electrically conductive member that extends from within its respective quartz tube 24 through the outlet 42 and into the microwave cavity 22. A resilient ring at each outlet may secure each microwave coupler in place. The resilient ring may be made from a dielectric material that exhibits a low loss to microwave energy at the frequency of interest, i.e. PTFE, polyetheretherketone (PEEK), nylon, ceramic, etc. In this embodiment, the microwave coupler is an elongate E-field probe. Other embodiments may use a loop coupler or the like.

To maximise the coupling of microwave power from the cavity, it would ordinarily be desirable to locate the microwave couplers opposite a field intensity maximum in the cavity. However, microwave couplers arranged in this way would then been spaced by a minimum of $\lambda_g/2$ along the applicator. At the microwave frequencies of interest, this spacing distance may be too far to create a uniform "blanket" of active agents from the quartz tubes. For example, at 2.45 GHz $\lambda_g/2$ is about 6 cm in an unloaded cavity. Accordingly, in this embodiment the microwave couplers are spaced apart by a distance less than $\lambda_g/2$. This means that they are aligned with portions of the guided wave having different field intensities. In order to equalise the amount of power coupled out by each microwave coupler, the amount by which the coupler projects into the cavity depends on the magnitude of the square of the field intensity. This is shown schematically as line 48 in FIG. 2. The coupler projects further into the cavity the lower the available power.

In addition, although not shown in line 48, the power available in the cavity generally decreases with distance away from the input 32. Accordingly, in addition to the projection length depends on the position with respect to the power maxima, the projection length also depends on the position within the cavity with respect to the input 32. For an equivalent position with respect to the nearest field maximum, the projection length may need to be increased with distance away from the input in order to extract the same amount of power. Electromagnetic field modelling using advanced EM field tools, such as Ansoft HFSS or CST Microwave Studio, may be used to determine the projection lengths. These EM modelling tools may also be used to determine the spacing (across and longitudinally) between adjacent couplers and be used to determine the position and type of stubs required to attempt to arrange the spacing between couplers to be equidistant or the same across the waveguide cavity and longitudinally. The projection lengths may also be determined through experimentation.

As noted above, tuning stubs may also be introduced into the waveguide cavity to adjust the fields set up inside the cavity in such a manner that the microwave power coupled out of the cavity or fed to each plasma generation region is substantially the same. The tuning stubs may be introduced into the same wall as the coupling probes, and/or may be introduced into the opposite wall, and/or may be introduced into one or both side walls. The tuning stubs may be metallic rods (screws or dowels) or dielectric posts made from a suitable material that exhibits a low loss characteristic at the microwave frequency of choice. The position of these tuning stubs/posts may be determined using EM field modelling tools or through experiment.

Figure 3:
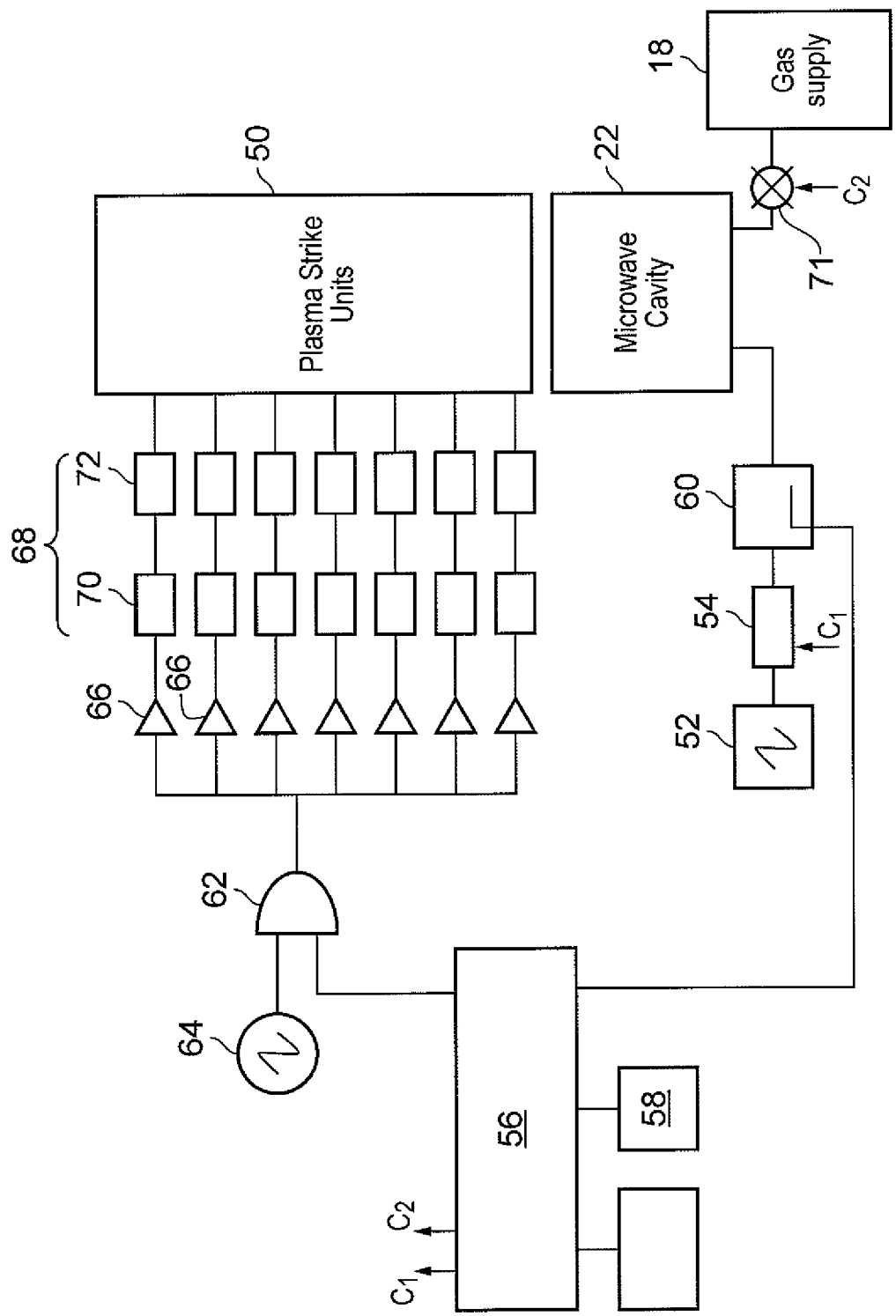
FIG. 3 is a block diagram showing the system components of plasma sterilisation apparatus that is an embodiment of the invention.

FIG. 3 shows a high level system diagram of the control components of the plasma sterilisation apparatus of the invention, which provide RF energy, microwave frequency energy and gas to the plasma strike zone. The plasma sterilisation apparatus comprises a microwave source 52 for generating the microwave frequency radiation. The microwave source may be one or more magnetrons, e.g. a 2M213 magnetron from Goldstar or another standard microwave oven magnetron made by Panasonic, Sony, etc. Each magnetron may generate microwave frequency radiation at a power of 700 W (continuous wave) or 3 kW (pulsed) or more.

A modulator 54 is connected to the output of the microwave source 52 via a suitable low loss connecter (e.g. flexible waveguide or the like). The output of the modulator 54 is connected to an input to the microwave cavity 22. The modulator 54 switches the output of the microwave source 52 to cause a pulsed microwave signal to be launched into the microwave cavity 22. The modulator 54 is controlled by control signal $C_1$ from system controller 56, which may be microprocessor, microcontroller or the like. The system controller 56 may set the pulse duration and duty cycle of the pulsed microwave signal. For example, the pulse duration may be 40 ms, with a 100 ms gap between pulses, i.e. has a duty cycle of 29%. If the power generated by the source is 50 W, this means that the average power level of each pulse delivered to the cavity is 14.3 W. If 49 plasma generation regions or zones are required for a waveguide applicator that covers one side of one hand, then the system would need to be capable of delivering 2450 W of peak power or 700 W of average power from each waveguide applicator. Assuming that four such applicators will be required in order to be able to cover both sides of both hands, then the peak microwave power required to be delivered into the plasma will be 12.25 kW and the average power 2.8 kW (assuming 100% source and power supply efficiency). The controller 56 may include a microwave feed monitor (not shown) for detecting the power level of microwave radiation delivered to the microwave cavity. Any of the pulse duration, duty cycle and power level output from the microwave source 52 may be adjustable (e.g. dynamically) to ensure that a desired level of power is delivered into the microwave cavity 52. The level of power may be selected by the apparatus operator, e.g. via a user interface 58 connected to the system controller 56.

A directional coupler 60 is connected between the modulator 54 and microwave cavity 22. The coupler 60 diverts a portion (e.g. 1% or less) of the forward microwave power for use in triggering the RF strike pulse. The coupled signal is processed by controller 56 to supply a RF strike window signal to one input of an AND gate 62. For example, the controller 56 may provide an analogue comparator whose output signal can be made to be close to the power supply rail when a reference signal is exceeded. The RF strike window signal is essentially a square pulse that sets the duration of the RF strike pulse (which may comprise a burst (i.e. discrete period) of RF energy). The other input of the AND gate 62 is connected to an RF source 64. The output of the AND gate 62 is therefore a burst of the RF energy having the frequency of the RF source and a duration corresponding to the RF strike window signal. An analogue solution for generating the RF strike window signal is discussed below with reference to FIG. 4.

The output of the AND gate 62 is connected to a plurality of gate driver circuits 66. Each gate driver circuit 66 is connected to drive a power MOSFET and transformer circuit 68 in which a high speed switch 70, e.g. a power MOSFET device, switches a voltage across the primary coil of a transistor 72 at the RF frequency. The secondary coil of the transformer 72 thereby generates a high voltage RF signal, which is supplied to a respective plasma strike zone as the RF strike pulse. In this embodiment, a gate driver circuit 66 and power MOSFET and transformer circuit 68 is provided for each plasma strike zone to ensure that a high enough voltage is generated in for each plasma strike zone. It may be preferable to use one RF strike pulse circuit to produce the RF strike pulse for a plurality of plasma generation regions or zones, i.e. 5, 10 or more RF coupled inputs to the plasma generation regions may be connected in parallel, but isolated using an inductor. In this arrangement, RF strike pulses may be coupled into the plasma generation regions or zones using a separate feed through capacitor and a series inductor.

The gas supply 18 in this embodiment is connected to the interior of microwave cavity 22 via a control valve 71, which is controlled by the system controller 56 via control signal $C_2$. Control signals $C_1$ and $C_2$ may be synchronised to ensure that the flow of gas is established in the plasma strike zones when the RE strike pulse and microwave energy are supplied.

Figure 4:
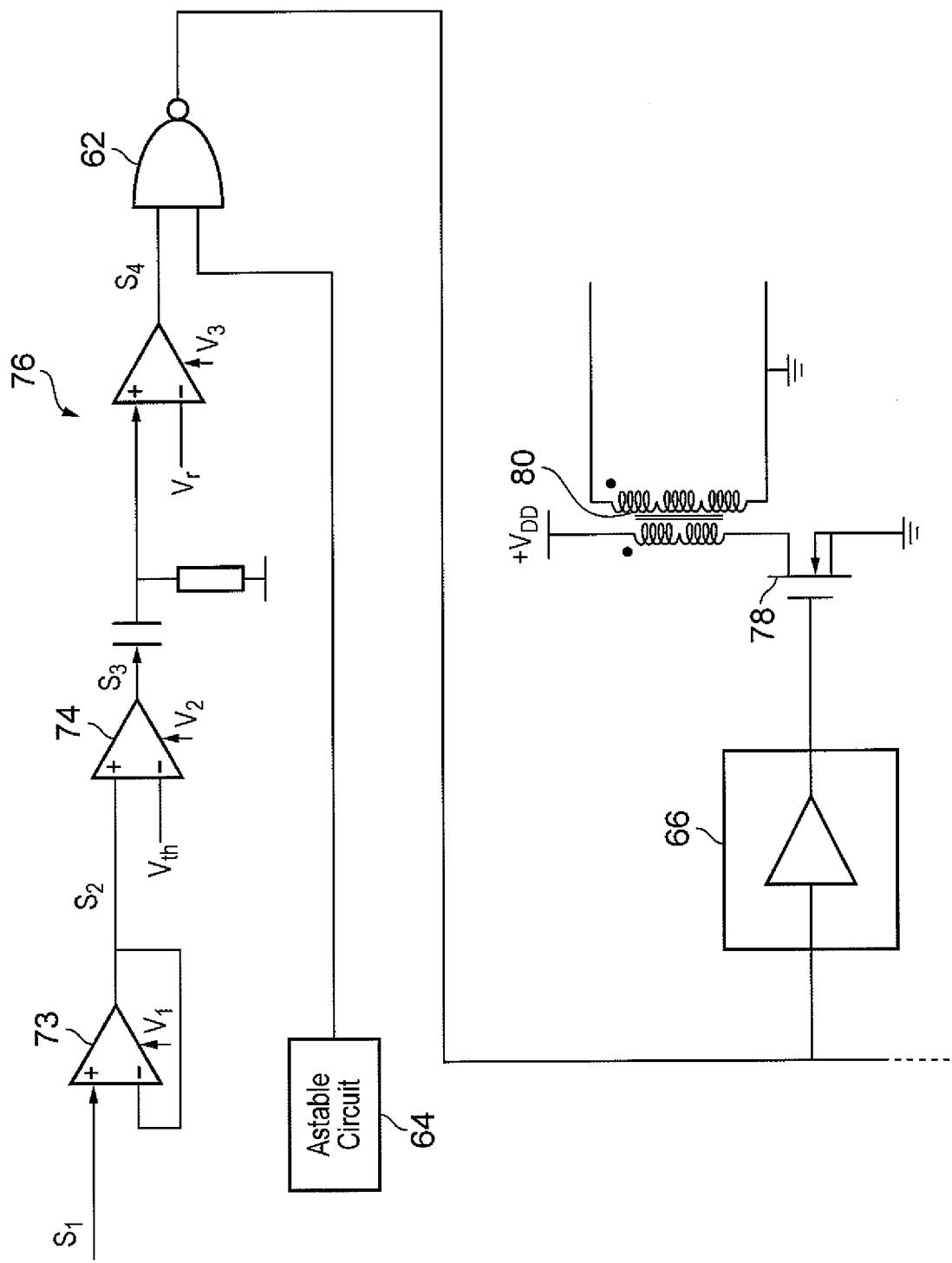
FIG. 4 is a strike signal generation circuit suitable for use in the plasma sterilisation apparatus of the invention.

FIG. 4 shows a detailed configuration of one embodiment of the strike signal generation circuitry. The NAND gate 62, the RF source 64, which in this embodiment is an astable circuit, and the inverting gate driver circuit 66 are given the same references numbers as in FIG. 3. In the arrangement shown in FIG. 4, the RF strike window signal is generated by using a threshold comparator 74 in conjunction with a differentiator 76. The input signal $S_1$ for the strike signal generation circuitry is derived from the portion of microwave energy from the directional coupler 60. The input signal $S_1$ is connected to a unity gain buffer 73 to ensure that the signal input to comparator 74 is not loaded. The resulting signal $S_2$ is conditioned to provide a constant voltage with a level that is close to or the same as the power supply rail voltage $V_2$ of the operational amplifier once the voltage seen at the non-inverting input to operational amplifier is greater than the threshold voltage $V_{th}$. This circuit provides a constant initial voltage level to the differentiator circuit. The trigger pulse is essentially a square wave pulse having same duration as the microwave pulse sent to the microwave cavity. For the purposes of the strike signal generation circuitry it is the rising edge of this signal that is of interest, as it is this that triggers a change in state of the threshold comparator 74. The output signal $S_2$ of the buffer 73 is input to threshold comparator 74, which generates an output signal $S_3$ if the voltage of signal $S_2$ is greater than threshold voltage $V_{th}$.

The output signal $S_3$ is input to differentiator 76, whose output signal $S_4$ has a voltage corresponding to the time derivative of the voltage of signal $S_3$. However, the duration of signal $S_4$ is limited by reference voltage $V_r$ input to the second comparator in the differentiator circuit. The result of this is that output signal S4 has a limited duration. Reference voltage $V_r$ can be set to establish the duration of the strike pulse.

As shown in FIG. 3, the output of the NAND gate 62 is connected to the gate driver circuit 66. The output of the inverting gate driver circuit is connected to the power MOSFET and transformer circuit, which is shown in FIG. 4 to comprise a MOSFET 78 connected to switch a voltage $+V_{DD}$ across the primary coil of a transformer 80. The secondary coil of the transformer 80 generates the RF strike signal, which is supplied to the corresponding plasma strike zone via a suitable feed structure, e.g. coaxial cable or the like.

Figure 5:
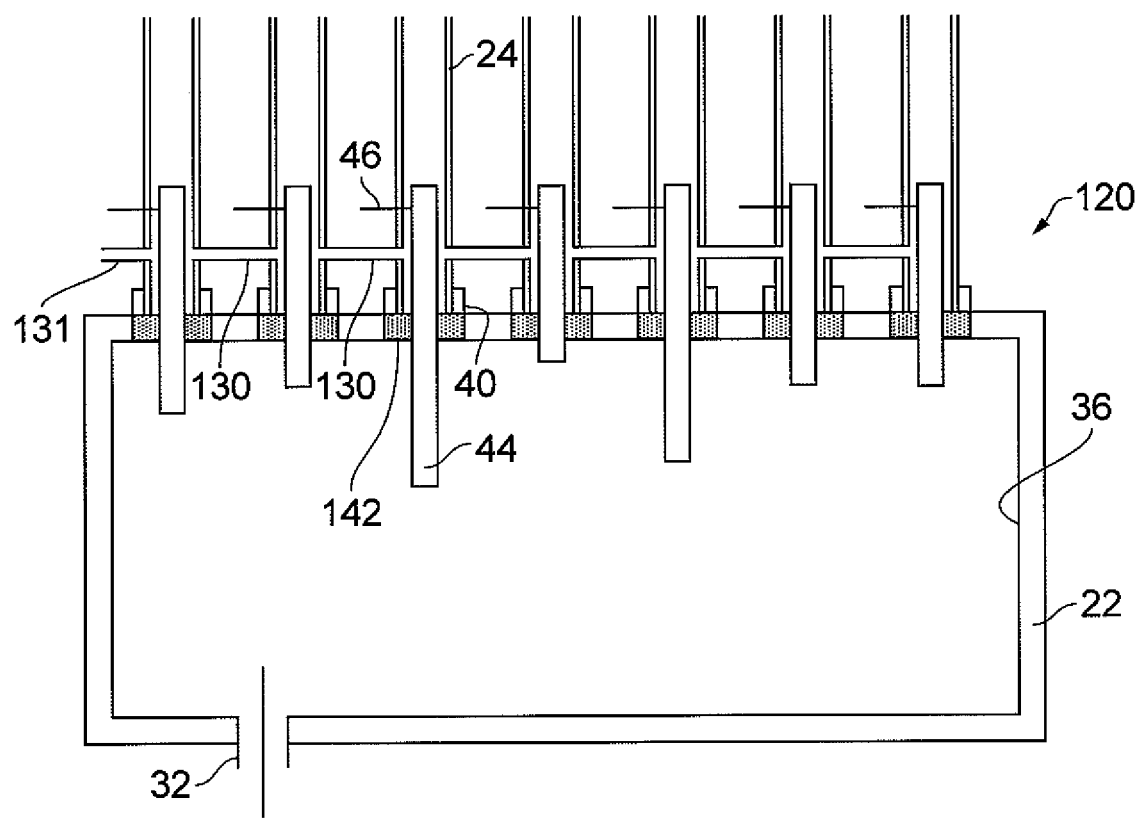
FIG. 5 is a schematic cross-sectional side view through plasma sterilisation apparatus that is another embodiment of the invention.

FIG. 5 shows a cross-sectional side view through a alternative representation of a plasma applicator 120 shown in FIG. 2. Features in common with FIG. 2 are given the same reference number and are not described again. The plasma applicator 120 in this embodiment differs from the embodiment shown in FIG. 2 in the way that the gas is supplied to the plasma strike zones. In this embodiment, the microwave cavity is closed; the gas flow does not pass therethrough. The microwave couplers 44 are mounted in the top face of the applicator 120 using impermeable fixtures 142, which both fix the applicator in place and seal the microwave cavity 22. The underside of the fixtures may be metallised to prevent microwave energy from escaping.

In this embodiment, the gas is supplied directly to each plasma strike zone through an inlet in the wall of the corresponding quartz tube 24. Each inlet may be connected in parallel to the gas supply, or, as shown in FIG. 5, a gas flow passage 130 may connected the interior of each quartz tube 24 with its neighbouring quartz tube. One of the quartz tubes, e.g. an endmost tube, comprises an inlet 131 for connecting to the gas supply (not shown). In this way the plasma strike zones are connected to the gas supply in series. One advantage of this arrangement is that it can ensure that the gas flow is equalized across the applicator.

Figure 6:
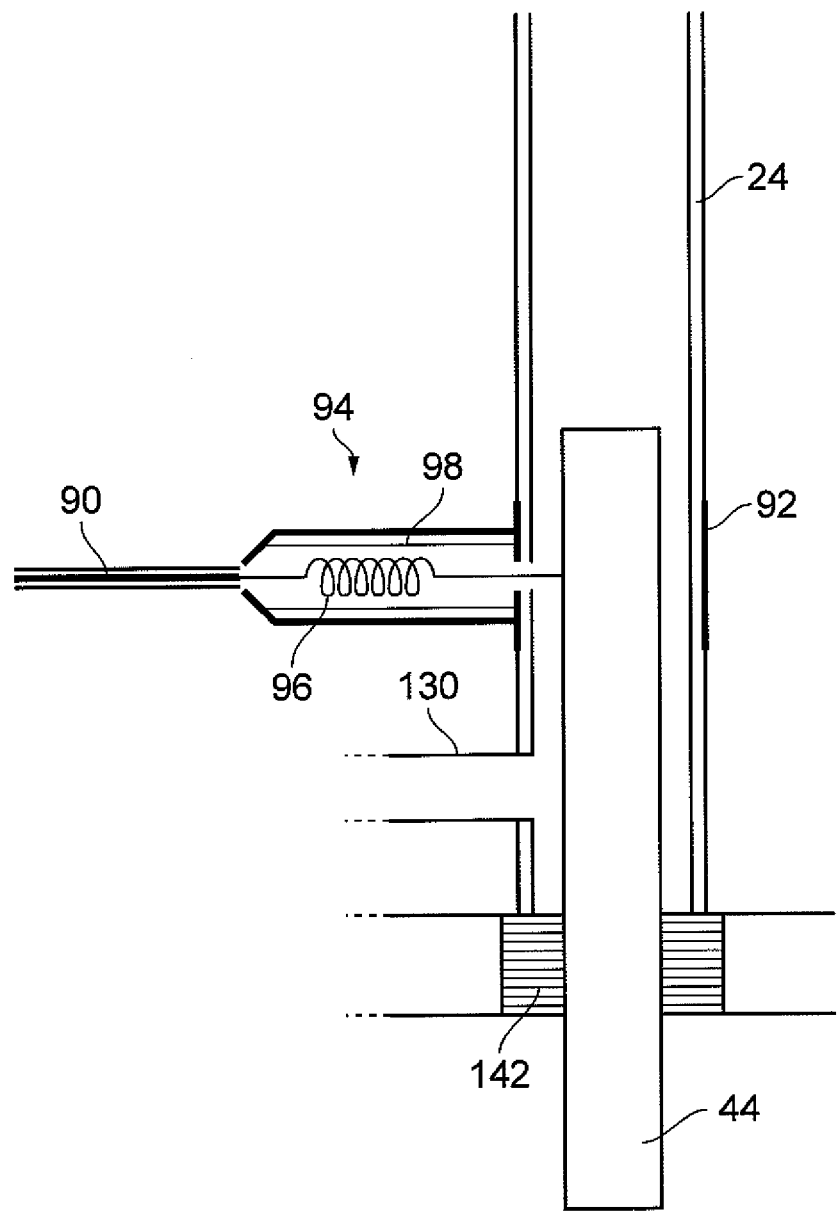
FIG. 6 is a schematic cross-sectional view of a plasma strike zone used in the plasma sterilisation apparatus of the invention.

FIG. 6 shows a more detailed view of a plasma strike zone inside a quartz tube 24 mounted on the top face of a plasma applicator as discussed above. Features in common with the arrangements described above are given the same reference number and are not described again. FIG. 6 shows a detailed example of the arrangement for launching the RF strike pulse into the plasma strike zone. The RF strike pulse is conveyed from the strike signal generation circuitry to the plasma strike zone via cable 90, which maybe a coaxial cable, a capacitive feed through, a wire contact or the like. If a coaxial cable is used, the centre conductor will be connected to coupler 44 via inductor 96. In this arrangement, the inner conductor of the coaxial cable 90 is electrically connected to the microwave coupler 44 in the quartz tube via inductor 96. The outer conductor of the coaxial cable 90, which may be grounded, is connected to an electrically conductive sleeve 92 formed around a portion of the outer surface of the quartz tube 24 that surrounds the end of the microwave coupler 44. The conductive sleeve 92 must fully surround conductor/coupler 44 and be electrically connected to the outer wall of the waveguide section/cavity 22. The length of conductive sleeve 92 or metallisation around quartz tube 24 must be such that microwave energy cannot radiate or escape from the plasma generation zone or region into free space or couple into tissue. The microwave coupler 44, quartz tube 24 and sleeve 92 therefore form a coaxial structure. The region inside the quartz tube 24 where gas flows through this coaxial structure is the plasma strike zone, since the high electric field caused by the RF strike pulse appears here.

A microwave blocking element 94 is connected between the coaxial cable 90 and the coaxial structure described above. The purpose of the microwave blocking element 94 is to prevent microwave energy coupled from the cavity by the microwave coupler 44 from travelling down the coaxial cable 90 towards the strike signal generation circuitry. In this embodiment, the microwave blocking element 94 comprises a coiled wire inductor 96 that is connected to the inner conductor of the coaxial cable 90 and insulated from the outer conductor of the coaxial cable 90 by an insulator 98. The inductor 96 may be made of a low loss material, such as silver.

The inductor 96 is particularly effective at blocking microwave frequency energy, e.g. 1 GHz or more.

Alternatively of additionally, one or more quarter wavelength stub may be connected to the outer conductor. The length of the stub is a quarter wavelength of the microwave frequency radiation. Including the stub may assist in prevent radiation of the microwave energy from the microwave blocking element 94.

Figure 7:
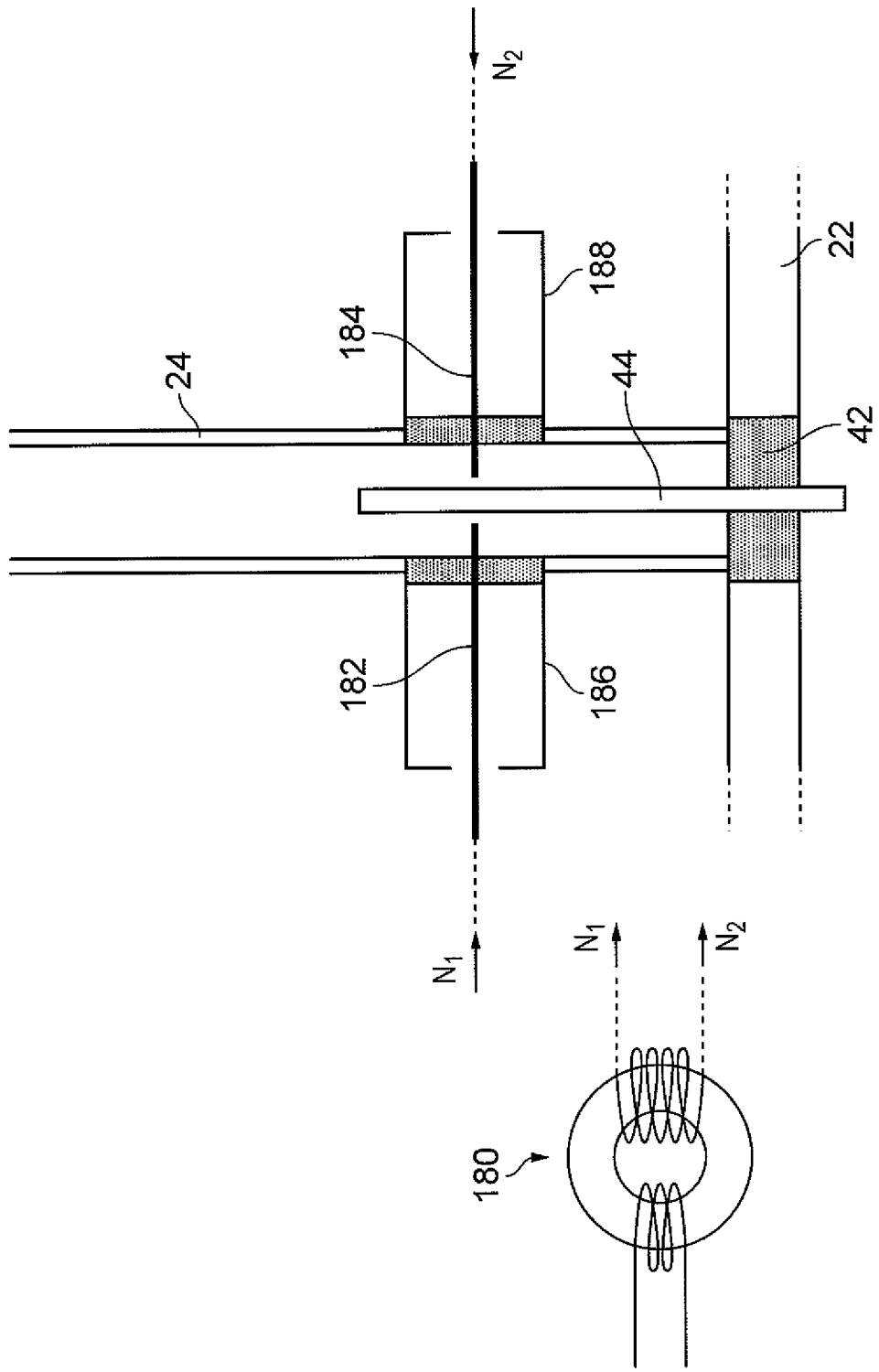
FIG. 7 is a schematic view of another plasma strike zone suitable for use in the plasma sterilisation apparatus of the invention.

FIG. 7 shows an alternative arrangement that can be used to couple the RF strike pulse into the plasma strike zone. In this arrangement, two non-contacting conductive needles 182, 184 are used to couple the RF strike pulse from the second winding of transformer 180 into the microwave coupler 44. The voltages $N_1$ and $N_2$ are arranged to be out of phase to create a large enough electric field at the plasma generation zone to enable plasma to be struck. Quarter-wavelength cylindrical stubs 186, 188 are used to ensure no microwave power is emitted from the applicator. The stubs are arranged to transform a short circuit at their proximal ends (where the needles enter) to an open circuit at the plasma strike zone. Seals 200 are used to ensure that gas cannot escape from the where the needles enter the plasma strike zone. This arrangement also ensures the E-field at the microwave coupler 44 is a maximum.

Figure 8A:
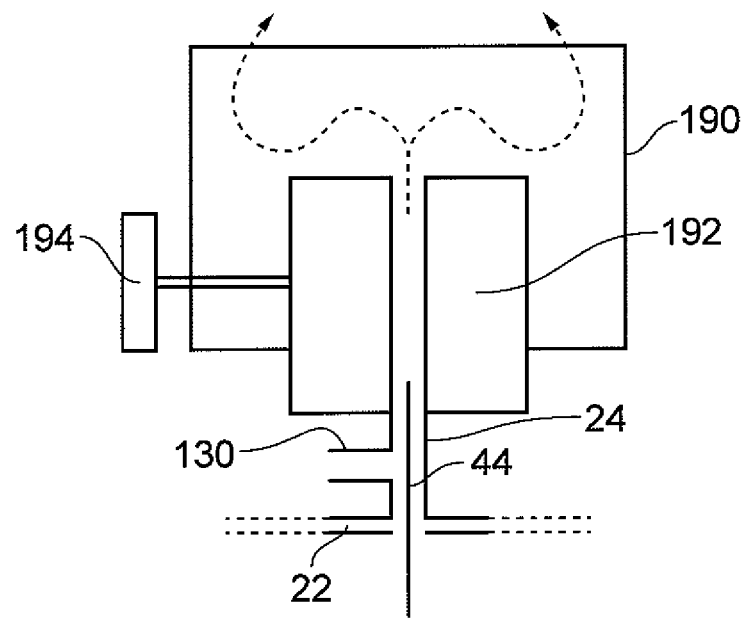
FIGS. 8A and 8B are respectively a schematic cross-sectional side view and a top view of a diffusion device connected to a plasma strike zone that is suitable for use with the plasma sterilisation apparatus of the invention.
Figure 8B:
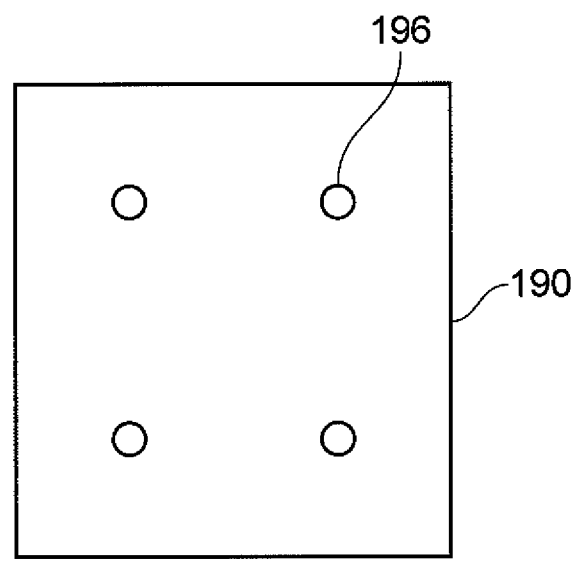

FIGS. 8A and 8B show the use of a diffusion device 190 which can be mounted over a quartz tube 24 to spread the active agents created by the plasma over a wider treatment area. The advantage of the diffusion device is that fewer plasma strike zones are needed to obtain the same coverage area for the active agents. Having fewer plasma strike zones may reduce the power demand of the appliance. In FIG. 8A, a quartz tube 24 projecting from the wall of the waveguide cavity 22 is shown as described above. A separate gas feed 130 provided gas to a volume enclosed by the quartz tube 24 in which the microwave energy is coupled from the cavity 22 by coupler 44 and an RF strike pulse is supplied as described above (the details are not shown for clarity). The quartz tube 24 is surrounded by a housing 192 which is received in a corresponding shaped aperture formed in the rear surface of the diffusion device 190. The housing 192 can be secured in the diffusion device 192 using locking screw 194. The length of the housing that is inserted into the diffusion device 190 can therefore be varied.

The diffusion device 190 itself is a chamber which encloses a volume around the outlet from the quartz tube. FIG. 8B shows a plan view of the top surface of the chamber, which is provided with four holes 196. The active agents created by the plasma therefore exit the diffusion device 190 through the holes, thereby spreading the effect of the plasma strike zone as indicated by the dotted arrows in FIG. 8A.

The invention claimed is:

1. Plasma sterilization apparatus comprising:
a microwave source;
a microwave cavity connectable to receive pulses of microwave frequency radiation from the microwave source;
a microwave coupler arranged to couple microwave energy out of the microwave cavity to a plasma strike zone, the plasma strike zone having a the gas flow path therethrough;
a gas feed connectable to supply ionizable gas to the gas flow path; and
a strike signal generation circuit arranged to deliver a pulse of radiofrequency (RF) energy to the plasma strike zone to generate a high electric field therein for striking a non-thermal plasma in ionizable gas present on the gas flow path,
wherein the strike signal generation circuit includes control circuitry arranged to use a detectable characteristic of a pulse of the microwave frequency radiation received in the microwave cavity to trigger generation of the pulse of RF energy.

2. Plasma sterilization apparatus according to claim 1 comprising a plurality of microwave couplers, each microwave coupler being mounted on the microwave cavity to couple microwave energy out of the microwave cavity to a respective plasma strike zone.

3. Plasma sterilization apparatus according to claim 2, wherein the plurality of microwave couplers are arranged in a 7×7 array on one surface of the microwave cavity.

4. Plasma sterilization apparatus according to claim 2 wherein the gas feed includes an inlet into the microwave cavity and one or more outlets from the microwave cavity, each outlet leading to a respective plasma strike zone, whereby the ionizable gas travels through the microwave cavity to reach the plasma strike zones.

5. Plasma sterilization apparatus according to claim 4, wherein each microwave coupler is secured in the respective outlet of its plasma strike zone by a gas-permeable connector.

6. Plasma sterilization apparatus according to claim 1 including a microwave signal probe connected at an input to the microwave cavity to couple a portion of the microwave frequency radiation received at the cavity to the control circuitry of the strike signal generation circuit.

7. Plasma sterilization apparatus according to claim 6, wherein the microwave signal probe is an E-field or H-field coupler.

8. Plasma sterilization apparatus according to claim 7, wherein the strike signal generation circuit comprises an RF strike circuit arranged to receive as an input a pulsed RF signal generated by the control circuitry using the portion of the microwave frequency radiation coupled from the cavity.

9. Plasma sterilization apparatus according to claim 8, wherein each RF strike circuit comprises a gate driver, a power MOSFET and a transformer.

10. Plasma sterilization apparatus according to claim 7, wherein the strike signal generation circuit comprises:
a plurality of RF strike circuits, each RF strike circuit being arranged to receive as an input a pulsed RF signal generated by the control circuitry using the portion of the microwave frequency radiation coupled from the cavity, and to output the pulse of RF energy to respective plasma strike zone, and
a RF signal splitter arranged to split the pulsed RF signal generated by the control circuitry to generate a separate input signal for each RF strike circuit.

11. Plasma sterilization apparatus according to claim 1, wherein the control circuitry is arranged to set a duration of the pulse of RF energy to 10 ms or less.

12. Plasma sterilization apparatus according claim 1, wherein the microwave source is arranged to deliver pulses of microwave frequency radiation having duration of 40 ms and a duty cycle of 29%.

13. Plasma sterilization apparatus according to claim 12, wherein the microwave source is a magnetron.

14. Plasma sterilization apparatus according to claim 1, wherein the plasma strike zone comprises:
a dielectric conduit extending out of the microwave cavity and defining the gas flow path,
a coaxial arrangement comprising an inner conductor located inside the dielectric conduit and an outer conductor separated from the inner conductor by the dielectric conduit, wherein the strike signal generation circuit is connected to the coaxial arrangement to generate a high electric field within the dielectric conduit upon delivery of the pulse of radiofrequency (RF) energy.

15. Plasma sterilization apparatus according to claim 14, wherein the strike signal generation circuit is connected to the coaxial arrangement via a microwave blocking element arranged to protect the strike signal generation circuit from the microwave energy in the plasma strike zone.

16. Plasma sterilization apparatus according to claim 15, wherein the strike signal generation circuit comprises a coaxial output line having an inner conductor connected to the inner conductor of the coaxial arrangement and an outer conductor connected to the outer conductor of the coaxial arrangement, wherein the microwave blocking element comprises an inductor on the inner conductor of the coaxial output line.

17. Plasma sterilization apparatus according to claim 14, wherein the inner conductor of the coaxial arrangement is at least part of the microwave coupler for the plasma strike zone.

18. Plasma sterilization apparatus according to claim 1, wherein the microwave coupler comprises a conductive member having a first portion protruding into the microwave cavity and a second portion extending outwardly from the microwave cavity to the plasma strike zone, and wherein a length of the first portion that is exposed in the microwave cavity is determined based on a field intensity of the microwave energy in the microwave cavity.

19. Plasma sterilization apparatus according to claim 18, wherein the microwave cavity is arranged to support substantially all the received microwave energy in a single waveguide mode, and wherein an amount of the first portion of the conductive member that is exposed in the microwave cavity is determined based on a position of the microwave coupler with respect to a field of a waveguide mode and a distance between the microwave coupler and a location at which the microwave energy is received in the cavity.

20. Plasma sterilization apparatus according claim 1 comprising metallic or dielectric tuning stubs mounted in the microwave cavity for controlling a level of power produced at an output of the microwave coupler.

21. Plasma sterilization apparatus according to claim 1, wherein the microwave cavity contains loading material.

22. Plasma sterilization apparatus according to claim 1, wherein the gas feed includes a separate inlet into the plasma strike zone.

23. Plasma sterilization apparatus according to claim 22, wherein the gas flow path of the plasma strike zone is connected in series to the gas feed.

24. Plasma sterilization apparatus according to claim 1 comprising a diffusion device on the gas flow path after the plasma strike zone, the diffusion device comprising an enclosure having a plurality of spaced-apart exit holes for spreading an output from the plasma strike zone.

25. An appliance for sterilizing hands, the appliance comprising:
a housing defining a hand-receiving recess between an upper inner surface and a lower inner surface;
a plurality of plasma sterilisation apparatuses according to claim 1 located in the housing and connected to receive pulses of microwave frequency radiation from the microwave source,
wherein the gas flow paths from the plasma strike zones of the plurality of plasma sterilization apparatuses terminate at either the upper inner surface or the lower inner surface, whereby plasma generated by the plurality of plasma sterilization apparatuses is arranged to impinge on a user's hand or hands when received in the hand-receiving recess.

26. An appliance according to claim 25, wherein the microwave source comprises a magnetron and a power splitter arranged to split an output from the magnetron into a plurality of microwave input signals, each microwave input signal being for a respective plasma sterilization apparatus.

27. An appliance according to claim 25, wherein the microwave source comprises a magnetron and a power multiplexer arranged to multiplex an output from the magnetron between the plurality of plasma sterilization apparatuses.

28. An appliance according to claim 25 having four plasma sterilization apparatuses arranged as a side-by-side upper pair at the upper inner surface and a side-by-side lower pair at the lower inner surface, whereby each plasma sterilization apparatus is directed at one side of one of the user's hands.

\* \* \* \* \*